US012697223B2

(12) United States Patent
de Villiers et al.

(10) Patent No.: US 12,697,223 B2
(45) Date of Patent: Aug. 4, 2026

(54) ARTIFICIAL INTERVERTEBRAL DISC WITH LOWER HEIGHT

(71) Applicant: Simplify Medical, Pty Ltd, San Diego, CA (US)

(72) Inventors: Malan de Villiers, Wapadrand (ZA); Neville Jansen, Pretoria (ZA); Yves Arramon, Sunnyvale, CA (US)

(73) Assignee: NuVasive, INC., San Diego, CA (US)

( * ) Notice: Subject to any disclaimer, the term of this patent is extended or adjusted under 35 U.S.C. 154(b) by 0 days.

(21) Appl. No.: 18/925,564

(22) Filed: Oct. 24, 2024

(65) Prior Publication Data

US 2025/0049575 A1      Feb. 13, 2025

Related U.S. Application Data

(63) Continuation of application No. 17/664,071, filed on May 19, 2022, now Pat. No. 12,138,171, which is a continuation of application No. 16/709,286, filed on Dec. 10, 2019, now Pat. No. 11,357,633, which is a continuation of application No. 15/841,738, filed on Dec. 14, 2017, now Pat. No. 10,517,733, which is a continuation of application No. 15/584,369, filed on May 2, 2017, now Pat. No. 9,883,945, which is a continuation of application No. 15/234,983, filed on Aug. 11, 2016, now Pat. No. 9,668,878, which is a continuation of application No. 14/285,411, filed on
(Continued)

(51) Int. Cl.
*A61F 2/44* (2006.01)
*A61F 2/30* (2006.01)

(52) U.S. Cl.
CPC ........ *A61F 2/30771* (2013.01); *A61F 2/4425* (2013.01); *A61F 2/4455* (2013.01); *A61F 2002/30649* (2013.01); *A61F 2002/30662*
(2013.01); *A61F 2002/30841* (2013.01); *A61F 2002/30884* (2013.01); *A61F 2002/30902* (2013.01); *A61F 2002/443* (2013.01); *A61F 2310/00407* (2013.01); *A61F 2310/00604* (2013.01); *A61F 2310/00796* (2013.01); *A61F 2310/0088* (2013.01)

(58) Field of Classification Search
CPC .......... A61F 2/44; A61F 2/442; A61F 2/4425; A61F 2/4611; A61F 2002/442
USPC ............................................. 623/17.11–17.16
See application file for complete search history.

(56) References Cited

U.S. PATENT DOCUMENTS

2006/0116768 A1* 6/2006 Krueger ............. A61B 17/1604
606/90
2009/0088850 A1* 4/2009 Froehlich .............. A61F 2/4425
623/17.15

\* cited by examiner

*Primary Examiner* — Eduardo C Robert
*Assistant Examiner* — Christina Negrellirodriguez

(57) ABSTRACT

The disclosure provides an intervertebral disc and related methods. An upper plate includes an upper vertebra contacting portion and a lower bearing surface portion. The upper vertebra contacting portion includes a convex central portion, and a fin or anchoring element with a transverse hole therethrough. A lower plate has a lower vertebra contacting surface and an upper bearing surface. The lower vertebra contacting surface of the lower plate has a convex central portion. The upper bearing surface has a concavity disposed opposite the convex central portion and wherein the convex central portion and the concavity have nesting curvatures. A core positioned between the upper and lower plates has rigid upper and lower convex surfaces configured to slide and translate over the bearing surfaces of the upper and lower plates.

16 Claims, 3 Drawing Sheets

Related U.S. Application Data

May 22, 2014, now Pat. No. 9,439,775, which is a continuation of application No. 12/400,221, filed on Mar. 9, 2009, now Pat. No. 8,764,833.

(60) Provisional application No. 61/069,048, filed on Mar. 11, 2008.

ARTIFICIAL INTERVERTEBRAL DISC WITH LOWER HEIGHT

CROSS-REFERENCES TO RELATED APPLICATIONS

This application is a continuation of U.S. patent application Ser. No. 17/664,071 filed May 19, 2022 (published as U.S. Pat. Pub. No. 2022-0273445), which is a continuation of U.S. patent application Ser. No. 16/709,286, filed Dec. 10, 2019 (now U.S. Pat. No. 11,357,633), which is a continuation of U.S. patent application Ser. No. 15/841,738, filed Dec. 14, 2017 (now U.S. Pat. No. 10,517,733), which is a continuation of U.S. patent application Ser. No. 15/584,369, filed May 2, 2017 (now U.S. Pat. No. 9,883,945), which is a continuation of U.S. patent application Ser. No. 15/234, 983, filed Aug. 11, 2016 (now U.S. Pat. No. 9,668,878), which is a continuation of U.S. patent application Ser. No. 14/285,411, filed May 22, 2014 (now U.S. Pat. No. 9,439, 775), which is a continuation of U.S. patent application Ser. No. 12/400,221 (now U.S. Pat. No. 8,764,833), filed Mar. 9, 2009, which claims priority to U.S. Provisional Application No. 61/069,048, filed Mar. 11, 2008, entitled "ARTIFICIAL INTERVERTEBRAL DISC WITH LOWER HEIGHT," the full disclosures of which are incorporated herein by reference in their entireties for all purposes.

BACKGROUND OF THE DISCLOSURE

The present disclosure relates to medical devices and methods. More specifically, the present disclosure relates to intervertebral disc prostheses.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different artificial intervertebral discs are currently being developed. For example, U.S. Patent Application Publication Nos. 2005-0021146, 2005-0021145, and 2006-0025862, which are hereby incorporated by reference in their entirety, describe artificial intervertebral discs. This type of intervertebral disc has upper and lower plates positioned against the vertebrae and a mobile core positioned between two plates to allow articulating, lateral and rotational motion between the vertebrae.

Another example of an intervertebral disc prostheses having a movable core is the CHARITE artificial disc (provided by DePuy Spine, Inc.) and described in U.S. Pat. No. 5,401,269. Other examples of intervertebral disc prostheses include MOBIDISC (provided by LDR Medical), the BRYAN Cervical Disc (provided by Medtronic Sofamor Danek, Inc.), and the PRODISC (from Synthes Stratec, Inc.) and described in U.S. Pat. No. 6,936,071. Some of these intervertebral discs are mobile core discs while others have a ball and socket type two piece design. Although existing disc prostheses provide advantages over traditional treatment methods, improvements are ongoing.

These known artificial intervertebral discs generally include upper and lower plates which locate against and engage the adjacent vertebral bodies, and a core for providing motion between the plates. The core may be movable or fixed, metallic, ceramic or polymer and generally has at least one convex outer surface which mates with a concave recess on one of the plates in a fixed core device or both of the plates for a movable core device. In order to implant these intervertebral discs, the natural disc is removed and the vertebrae are distracted or forced apart in order to fit the artificial disc in place. Depending on the size of the disc space, many of the known artificial discs have a height which is higher than desired resulting in an unnaturally over distracted condition upon implantation of the disc. For example, a smallest height disc available can be about 10-13 mm for lumbar discs and about 5-6 mm for cervical discs.

Currently available artificial intervertebral discs do not provide a desired low profile for some patients with smaller disc heights. The use of an artificial disc which is too large for a patient's disc space can result in limited mobility of the disc. An improperly sized artificial disc can also move out of place in the disc space. Accordingly, it would be desirable to provide a lower height disc which mimics more closely the natural anatomy for smaller patients.

In addition, the vertebral body contacting surfaces of many of the known artificial discs are flat. This flat configuration does not generally match the surfaces of the vertebral bodies resulting in less than ideal bone to implant contact surfaces. It would be desirable to provide a more anatomically shaped vertebral body contacting surface for an artificial disc.

Therefore, a need exists for an improved artificial intervertebral disc with a lower disc height and more anatomically shaped upper surface.

BRIEF SUMMARY OF THE DISCLOSURE

According to the disclosure there is provided an intervertebral prosthesis for insertion between adjacent vertebrae, the prosthesis comprising upper and lower prosthesis plates with domed outer surfaces locatable against adjacent vertebral bodies.

In accordance with another aspect of the disclosure, an intervertebral disc includes an upper plate having an upper vertebra contacting surface and a lower bearing surface and a lower plate having a lower vertebra contacting surface and an upper surface. The upper surface of the upper plate has a convex central portion and at least one anchoring element extending from an upper surface of the convex central portion. The lower bearing surface of the upper plate has a concavity disposed opposite the convex central portion. The lower surface of the lower plate has a convex central portion and the upper bearing surface of the lower plate has a concavity disposed opposite the convex central portion. A core is positioned between the upper and lower plates, the core having upper and lower convex surfaces configured to mate with the bearing surfaces of the upper and lower plates.

In accordance with a further aspect of the disclosure, an intervertebral disc includes a first plate having a first vertebrae contacting surface and a bearing surface opposite the first vertebrae contacting surface, and a second plate having a second vertebrae contacting surface and an opposite surface and wherein the second plate articulates with respect to the first plate. The first vertebrae contacting surface of the first plate has a convex central dome shaped portion and at least one anchoring fin extending from an outer surface of the convex central dome shaped portion, and the bearing surface of the first plate has a concavity directly opposed to the convex central portion.

In accordance with an additional aspect of the disclosure, an intervertebral disc includes an upper plate having an upper vertebra contacting surface and a lower surface, and a lower plate having a lower vertebra contacting surface and an upper surface, and the upper plate articulates with respect to the lower plate. The upper surface of the upper plate has at least one anchoring fin extending from the upper surface of the upper plate and the lower surface of the lower plate has at least one anchoring fin extending from the lower surface of the lower plate. A plurality of teeth are positioned in a symmetrical pattern on opposite sides of the anchoring fins of the upper and lower plates, the plurality of teeth each having a first surface and a second surface opposite the first surface, wherein the first surface is formed at an angle of less than 40 degrees with respect to the vertebra contacting surfaces and the second surface is formed at an angle of more than 50 degrees with respect to the vertebra contacting surfaces. A plurality of serrations surround the plurality of teeth, wherein the plurality of serrations have a height at least 25 percent lower than a height of the teeth.

Additional embodiments of the disclosure provide an intervertebral disc including: an upper plate having: an upper vertebra contacting portion and a lower bearing surface portion, wherein the upper vertebra contacting portion of the upper plate includes: a convex central portion, a fin formed integrally with and extending outward from an upper surface of the convex central portion to define a height above the upper surface, the height being greater than a width of the fin, wherein the lower bearing surface portion has a concavity disposed opposite the convex central portion and wherein the convex central portion and the concavity have nesting curvatures, and a transverse hole extending at least partially through the width of the fin, and sized for bone ingrowth; a lower plate having a lower vertebra contacting surface and an upper bearing surface; and, wherein the lower vertebra contacting surface of the lower plate has a convex central portion, and wherein the upper bearing surface has a concavity disposed opposite the convex central portion and wherein the convex central portion and the concavity have nesting curvatures; and a rigid core positioned between the upper and lower plates, the core having rigid upper and lower convex surfaces configured to slide and translate over the bearing surfaces of the upper and lower plates.

Further embodiments of the disclosure provide an intervertebral disc including: an upper plate having: an upper vertebra contacting portion and a lower bearing surface portion, wherein the upper vertebra contacting portion of the upper plate includes: a convex central portion, an anchoring element formed integrally with and extending outward from an upper surface of the convex central portion to define a height above the upper surface, and extending along an axis substantially aligned with a centerline axis of the core, wherein the lower bearing surface portion has a concavity disposed opposite the convex central portion and wherein the convex central portion and the concavity have nesting curvatures, and a transverse hole extending at least partially through a width of the anchoring element, and sized for bone ingrowth; a lower plate having a lower vertebra contacting surface and an upper bearing surface; and, wherein the lower vertebra contacting surface of the lower plate has a convex central portion, and wherein the upper bearing surface has a concavity disposed opposite the convex central portion and wherein the convex central portion and the concavity have nesting curvatures; and a rigid core positioned between the upper and lower plates, the core having rigid upper and lower convex surfaces configured to slide and translate over the bearing surfaces of the upper and lower plates.

Still further embodiments of the disclosure provide a method of implanting an artificial intervertebral disc between adjacent spinal vertebrae in place of a damaged disc, the method including: providing an artificial intervertebral disc including: an upper plate having: an upper vertebra contacting portion and a lower bearing surface portion, wherein the upper vertebra contacting portion of the upper plate includes: a convex central portion, a fin formed integrally with and extending outward from an upper surface of the convex central portion to define a height above the upper surface, the height being greater than a width of the fin, wherein the lower bearing surface portion has a concavity disposed opposite the convex central portion and wherein the convex central portion and the concavity have nesting curvatures, and a transverse hole extending at least partially through the width of the fin, and sized for bone ingrowth; a lower plate having a lower vertebra contacting surface and an upper bearing surface; and, wherein the lower vertebra contacting surface of the lower plate has a convex central portion, and wherein the upper bearing surface has a concavity disposed opposite the convex central portion and wherein the convex central portion and the concavity have nesting curvatures; and a rigid core positioned between the upper and lower plates, the core having rigid upper and lower convex surfaces; inserting the artificial intervertebral disc including the upper and lower plates and core together into a space between the adjacent spinal vertebrae; allowing the upper and lower plates to slide and translate over the rigid upper and lower convex surfaces of the core. Other features of the disclosure are set forth in the appended claims.

DETAILED DESCRIPTION OF THE DISCLOSURE

Figure 1:
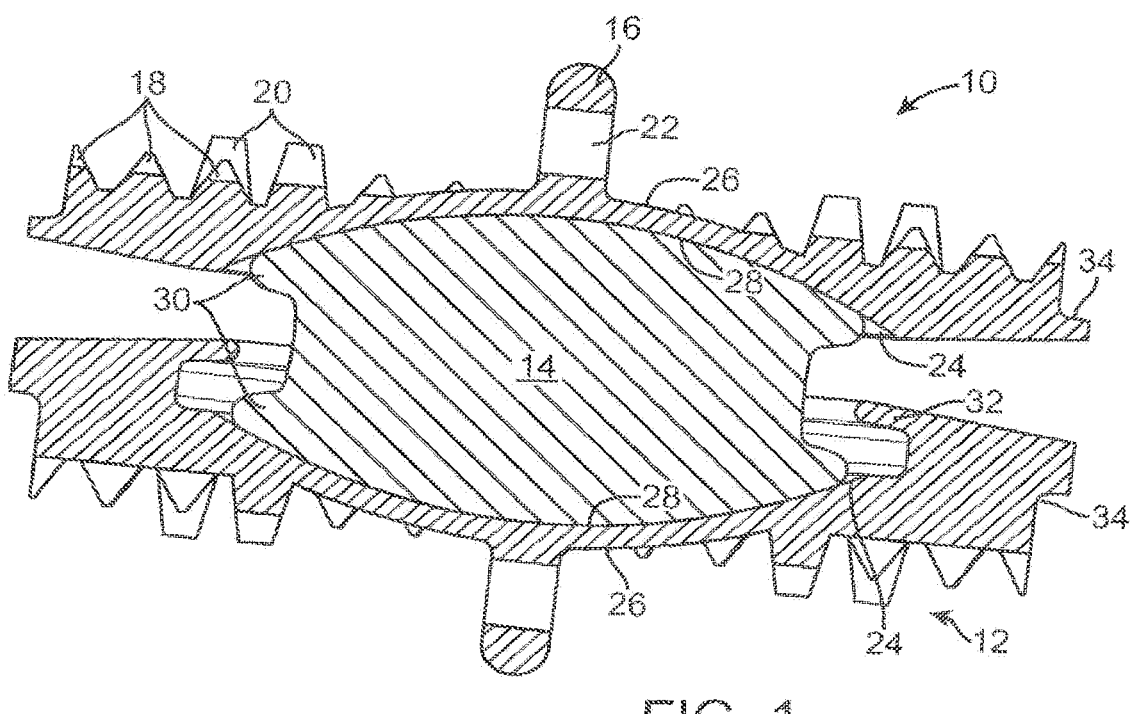
FIG. 1 is a cross sectional view of an intervertebral disc according to one embodiment of the present disclosure.
Figure 2:
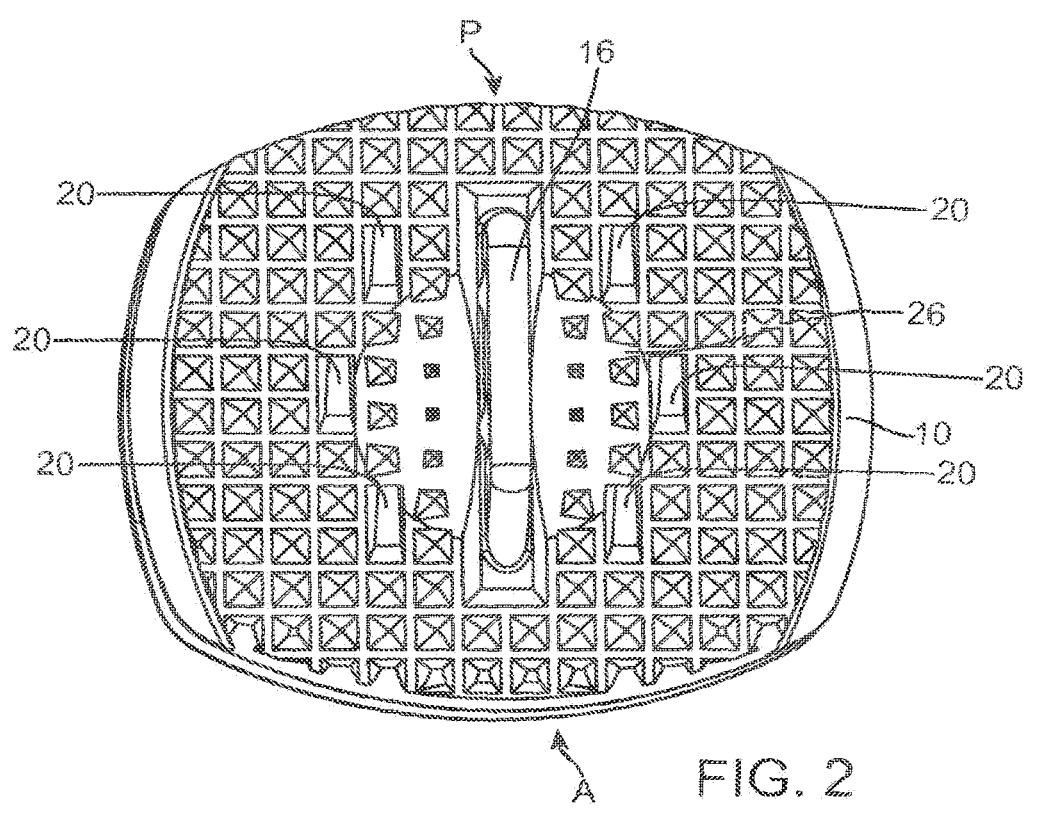
FIG. 2 is a top view of the intervertebral disc of FIG. 1.
Figure 3:
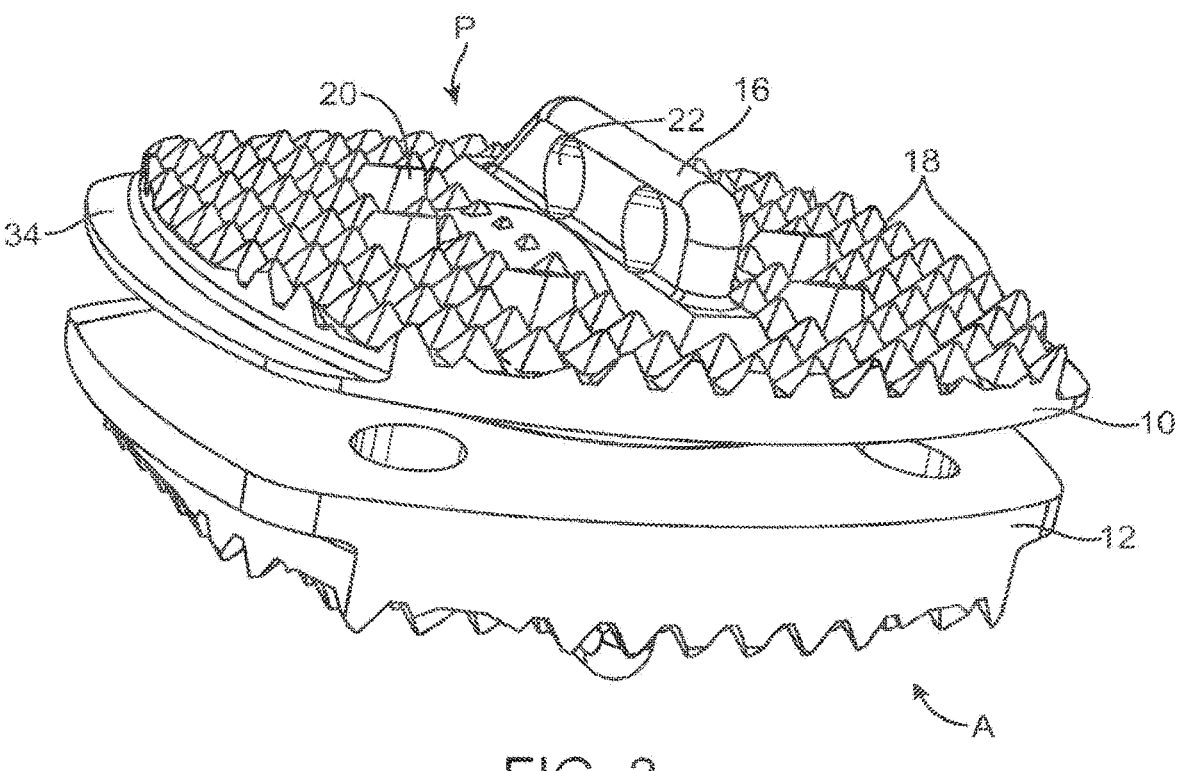
FIG. 3 is a perspective view of the intervertebral disc of FIG. 1.

FIGS. 1-3 illustrate an intervertebral disc having an upper plate 10, a lower plate 12, and a core 14. The upper and lower plates 10, 12 include outer vertebral body contacting surfaces which are provided with attachment enhancing features to ensure bone integration. The attachment enhancing features shown include one or more fins 16, serrations 18 and teeth 20. The fin 16 can be an elongate fin pierced by one or more transverse holes 22. The disc can be inserted posteriorly into the patient from an anterior access, such that fin 16 can enter a groove in one of the vertebrae as a posterior side P of the intervertebral disc enters the intervertebral space followed by an anterior side A of the intervertebral disc. An opposite surface of the plates from the vertebral body contacting surfaces is formed with a recess 24 which serves as a bearing surface for the core 14. In order to form an intervertebral disc with a lower disc height, at least one of the recesses 24 is provided opposite a corresponding dome shaped portion 26 on the vertebral body contacting surfaces. This allows the plates 10, 12 to be formed with a thinner profile for a smaller overall disc height.

In addition to providing a lower overall height to the artificial disc, the dome shaped portion 26 of the plates also provides a more anatomically shaped outer vertebral body contacting surface. The surfaces of the vertebral bodies are commonly not flat, but instead have a slight dish shape to their center portion. The dome shaped portion 26 fits well into this dish shape of the vertebrae providing better bone contact and improved bone integration.

The core 14 can be formed as a circular disc shaped member with upper and lower bearing surfaces 28 which match the curvature of the recesses 24. The core 14 also has an annular rim 30 which cooperates with a retention feature 32 on at least one of the discs to retain the core between the plates when the intervertebral disc is implanted between the vertebrae of a patient. The core 14 is moveable with respect to both the upper and lower discs to allow articulation, translation and rotation of the upper and lower plates with respect to one another. The core surfaces 28 and recess surface 24 have the same radius of curvature which may vary depending on the size of the intervertebral disc.

In the embodiment shown in FIGS. 1-3 a single central fin 16 is provided on each of the plates 10, 12 extending in an anterior posterior direction with an angled posterior edge for aiding in insertion. This embodiment is particularly useful for insertion from an anterior side of the intervertebral disc space. Alternatively, two or more fins 16 can also be provided on each plate. In one example, a single fin can be provided on one plate while double fins can be symmetrically arranged on the other plate to achieve a staggered arrangement particularly useful for multi-level disc implant procedures. This staggered arrangement prevents the rare occurrence of vertebral body splitting by avoiding cuts to the vertebral body in the same plane for multi-level implants. The orientation of the fin(s) 16 can also be modified depending on the insertion direction for the intervertebral disc. In alternative embodiments, the fins 16 may be rotated away from the anterior-posterior axis, such as in a lateral-lateral orientation, a posterolateral-anterolateral orientation, or the like for implantation in the associated directions.

The fins 16 are configured to be placed in slots in the vertebral bodies. In one embodiment, the fins 16 are pierced by transverse holes 22 for bone ingrowth. The transverse holes 22 may be formed in any shape and may extend partially or all the way through the fins 16. Preferably, the fins 16 each have a height greater than a width and have a length greater than the height.

The fins 16 provide improved attachment to the bone and prevent rotation of the plates in the bone. In some embodiments, the fins 16 may extend from the surface of the plates 10, 12 at an angle other than 90°. For example on one or more of the plates 10, 12 where multiple fins 16 are attached to the surface the fins may be canted away from one another with the bases slightly closer together than their edges at an angle such as about 80-88 degrees. The fins 16 may have any other suitable configuration including various numbers, angles, and curvatures, in various embodiments. In some embodiments, the fins 16 may be omitted altogether.

Figure 4:
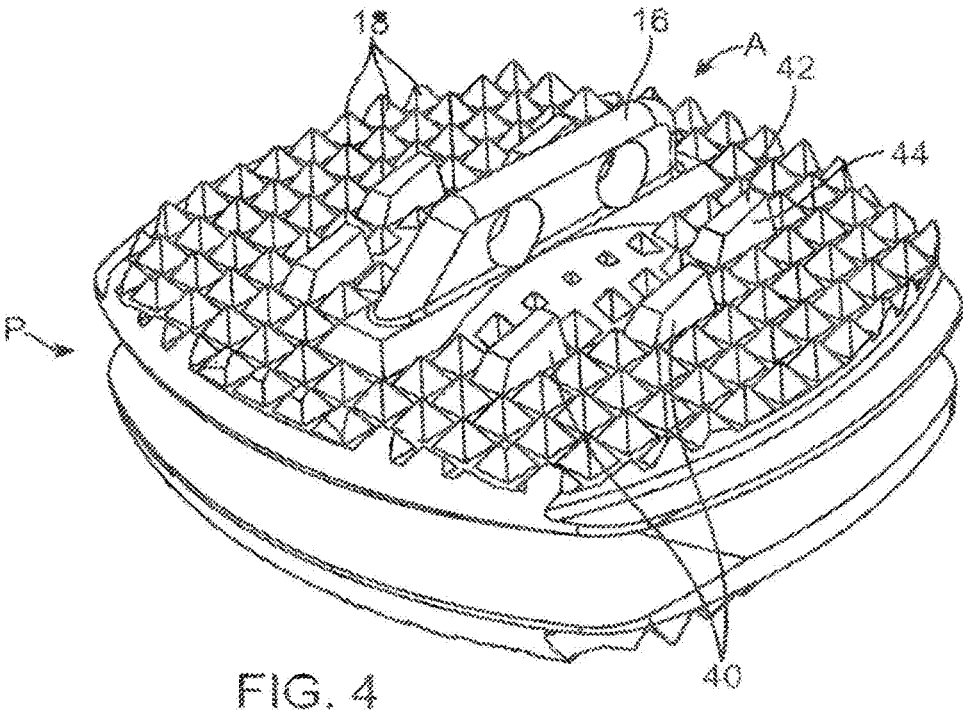
FIG. 4 is a perspective view of an intervertebral disc according to another embodiment of the disclosure.

The teeth 20 shown in FIG. 1 to FIG. 3 include six teeth arranged in a chevron shape with the narrow portion of the chevron located on a posterior side of the plates 10, 12. However, other numbers of teeth and teeth arrangements may also be used. For example, the teeth 20 may be arranged, as shown in FIG. 4, in an alternating arrangement such that the first and third teeth on each side are aligned and located closer to the midline of the disc while the central tooth is located further from the midline (a diamond shape pattern). The teeth can be positioned in varying numbers and arrangements depending on the size and shape of the plate used.

Figure 2A:
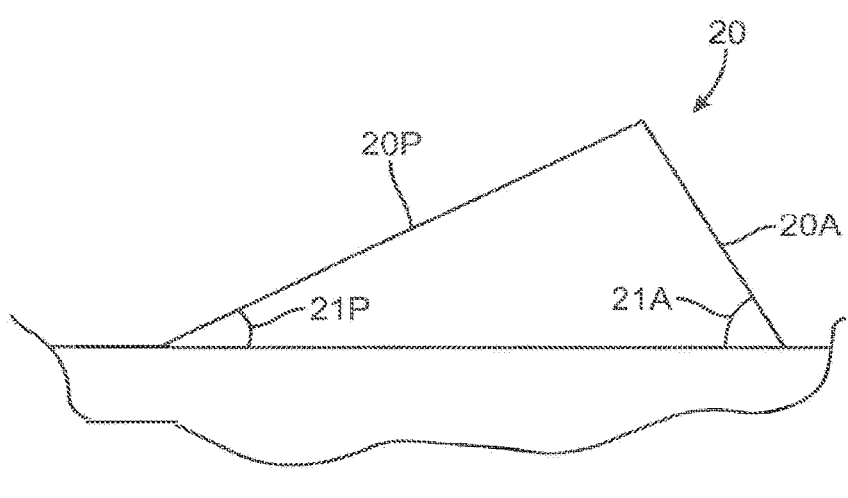
FIG. 2A is a side profile view of the teeth shown in FIG. 1.

The teeth 20 as shown in FIG. 1 to FIG. 3 have an elongated shape with opposite triangular side surfaces. As shown most clearly in FIG. 2A, each of teeth 20 comprises a posterior surface 20P and anterior surface 20A. In the embodiment of FIGS. 1-3, the teeth each have posterior surface 20P opposite anterior surface 20A, wherein the posterior surface is formed at an angle 21P of less than 40 degrees with respect to the vertebra contacting surfaces of the plates 10, 12, and the anterior surface 20A is formed at an angle of more than 50 degrees with respect to the vertebra contacting surfaces. Preferably, the posterior surface 21P is formed at an angle of about 5 to about 30 degrees, while the anterior surface 21A is formed at an angle of about 70 to about 90 degrees. In addition, the anterior surface 21A can be canted in the anterior direction to provide a tooth in the form of a barb. In this way, the posterior surface 21P provides minimal resistance to insertion while the anterior surface 21A prevents backing out of the disc.

Although wedge shaped teeth are shown, other teeth shapes may also be used, for example pyramidal, conical, rectangular and/or cylindrical teeth.

Referring now to FIG. 4, vertebrae contacting surfaces may comprise finlets 40. Finlets 40 can be somewhat larger than teeth and differ from teeth in that they have an additional top surface. The finlets 40 may have a tapered top surface 42 and larger base portion 44. The teeth 20 and/or finlets 40 may have a height which is preferably greater than that of the serrations. The teeth and/or finlet heights can be about 0.5-3 mm, preferably about 1-2 mm and more preferably about 1.1-1.5 mm. In the example of FIG. 4, the finlets 40 have an anterior surface formed at an angle of about 70 to 90 degrees, preferably about 80 degrees a posterior surface formed at an angle of about 50-70 degrees, preferably about 60 degrees, and a top surface formed at an angle of about 2-20 degrees, each with respect to the vertebra contacting surfaces.

The dome shaped portion(s) 26 on the vertebral body contacting surfaces are provided to allow the core 14 to be recessed further into the upper and lower plates 10, 12. The dome shaped portion preferably has a diameter less than a diameter of the core, i.e. less than about 20 mm for a lumbar disc and less than about 10 mm for a cervical disc. In one preferred embodiment, the external dome 26 has a diameter of about 10-20 mm for lumbar and about 5-10 mm for cervical. The dome in one embodiment has a height of about 0.5-3 mm above a plane formed by the vertebral body contacting surfaces of the plates at the base of the serrations, when serrations are present. Preferably, the dome height is about 0.7-2 mm.

In the embodiment shown in FIGS. 1-3, some of the serrations 18 are located on the surface of the dome shaped portion 26, with the tops of the serrations even with the serrations which are not positioned on the dome. Alternatively, the serrations 18 on the dome 26 can extend somewhat higher than the other serrations on the plates or serrations can be omitted on the dome shaped portion. The serrations 18 as shown are pyramid shaped serrations extending in mutually orthogonal directions, however, other shapes may also be used. The serrations have a height of about 0.5-1 mm and a width about equal to their height. With passage of time, firm connection between the plates 10, 12 and the vertebrae will be achieved as bone tissue grows over the serrated finish. Bone tissue growth will also take place about the fins 16 and through the holes 22 therein, further enhancing the connection which is achieved.

Other geometries of bone integration structures may also be used including teeth, grooves, ridges, pins, barbs or the like. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surfaces of the plates 10, 12 may be provided with a rough microfinish formed by blasting with aluminum oxide microparticles or the like to improve bone integration. In some embodiments, the outer surface may also be titanium plasma sprayed or HA coated to further enhance attachment of the outer surface to vertebral bone.

The core 14 according to the embodiments of FIGS. 1-4 can be retained in the lower plate 12 by retention feature 32 comprising a retention ring that protrudes inwardly from an edge of the lower plate 12 at an edge of the lower bearing surface of the plate. Although a circumferential core retaining feature is shown, other core retaining features may also be used including at least those shown in U.S. Patent Publication Nos. 2005/0251262, 2005/0021146, and 2005/0021145, which are incorporated herein by reference in their entirety.

Although the core 14 has been shown as circular in cross section with spherically shaped bearing surfaces 28, other bearing surface shapes may be used including oval, elliptical, or kidney bean shaped. These non-circular shaped cores can be used to limit rotational motion between the upper and lower plates 10, 12. The bearing surface shapes may also vary from the spherical shapes shown and may vary between the upper and lower surfaces of the core. Other bearing surface shapes include cylindrical, elliptical, trough shaped, groves, flat surfaces, or the like. Although the core 14 and plates 10, 12 have been shown as solid members, the core and plates may be made in multiple parts and/or of multiple materials. The core can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

The intervertebral disc according to the present disclosure provides articulation in two directions as well as rotation. The plates 10, 12 are provided with grooves 34 at their lateral edges for use in grasping the disc by an instrument to facilitate holding and manipulation of the disc for insertion or removal of the disc. The grooves 34 allow the plates 10, 12 to be grasped and inserted simultaneously in a locked orientation.

The upper and lower plates 10, 12 may be formed from titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. The bearing surfaces or recesses 24 are concavely, spherically curved and can have a hard coating such as a titanium nitride finish. The plates 10, 12 may be treated with aluminum oxide blasting followed by a titanium plasma spray to improve bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof to optimize imaging characteristics. Any suitable technique may be used to couple materials together, such as snap fitting, slip fitting, lamination, interference fitting, use of adhesives, welding and/or the like.

Figure 5:
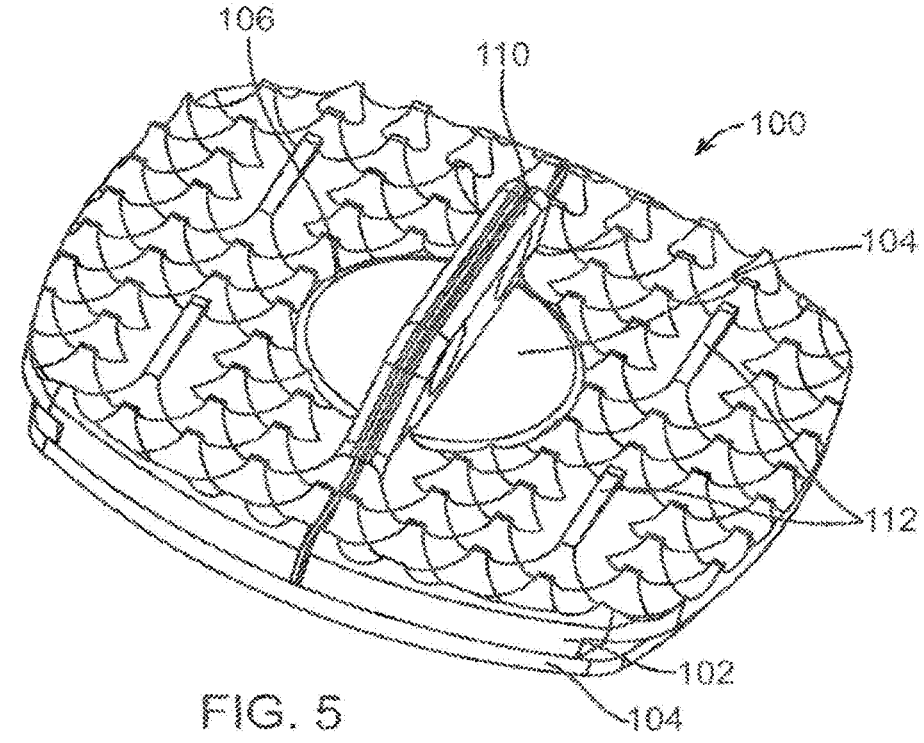
FIG. 5 is a perspective view of an intervertebral disc plate according to another embodiment of the disclosure with a bearing surface insert.

FIG. 5 illustrates an alternative embodiment of an intervertebral disc plate 100 having a metallic vertebral body contacting portion 102 and a bearing surface insert 104 formed of PEEK or other MRI compatible material. The PEEK insert 104 includes the bearing surface (not shown) and has a dome shaped central portion. The metallic portion 102 includes a central circular opening 106 which can be of any shape and accommodates a portion of the PEEK insert 104. The metallic portion 102 may be formed in two parts and welded around the PEEK insert 104 to form a firm connection between the metallic and PEEK portions of the plate. The PEEK insert provides the advantage of MRI compatibility while the metallic vertebral body contacting portion 102 provides a superior surface for bone integration and includes one or more fins 110, finlets 112, and serrations 114 as described with respect to the other embodiments described herein.

Each of the artificial intervertebral discs as described herein is surgically implanted between adjacent spinal vertebrae in place of a damaged disc. Those skilled in the art will understand that the surgical technique for implanting the artificial discs involves partial or total removal of the damaged disc and distraction of the adjacent vertebrae by forcibly separating the vertebrae from one another to provide the necessary space for insertion of the disc. The plates 10, 12 are slipped into place between the vertebrae with their fins 16 entering slots cut in the opposing vertebral surfaces to receive them. The plates may be inserted simultaneously with or without the core. After partial insertion of the disc, the individual plates 10, 12 can be further advanced independently or together to a final position. Once the disc has been inserted, the vertebra move together to hold the assembled disc in place.

The vertebral contacting surfaces of the plates 10, 12 including the teeth 20 and the serrations 18 locate against the opposing vertebrae and, with passage of time, firm connection between the plates and the vertebrae will be achieved as bone tissue grows over the serrated finish. Bone tissue growth will also take place about the fins 16 and through the holes 22 therein, further enhancing the connection which is achieved.

While the exemplary embodiments have been described in some detail, by way of example and for clarity of understanding, those of skill in the art will recognize that a variety of modifications, adaptations, and changes may be employed. Hence, the scope of the present disclosure should be limited solely by the appended claims.

What is claimed is:

1. An intervertebral disc comprising:

an upper plate having an upper vertebra contacting portion and a lower bearing surface portion, wherein the upper plate includes a convex central portion and is made of PEEK;

a lower plate having a lower vertebra contacting portion and an upper bearing surface portion, wherein the lower plate is made of PEEK; and a rigid core positioned between the upper and lower plates, the core configured to slide and translate over the upper bearing surface and the lower bearing surface portion, wherein the rigid core is ceramic, wherein the upper plate includes a fin disposed on the upper vertebra contacting portion that has a length greater than a height, wherein the upper vertebral contacting surface and the lower vertebral contacting surface include three finlets on opposing sides of the fin, wherein the finlets extend in height greater than teeth positioned on the upper vertebral and lower vertebral contacting surfaces, and each finlet includes top surface, wherein each of the finlets have an anterior surface formed at an angle of about 70 to 90 degrees, preferably about 80 degrees, a posterior surface formed at an angle of about 50-70 degrees, preferably about 60 degrees, and the top surface formed at an angle of about 2-20 degrees, each with respect to the upper and lower vertebral contacting portions.

2. The intervertebral disc of claim 1, wherein the upper vertebra contacting portion includes a metal and the lower bearing surface portion includes an MRI compatible material.

3. The intervertebral disc of claim 1, further comprising a plurality of teeth on the upper vertebra contacting portion of the upper plate and the lower vertebra contacting surface of the lower plate.

4. The intervertebral disc of claim 1, wherein each of the upper plate and the lower plate include dome shaped portions convex central portions.

5. The intervertebral disc of claim 4, wherein the dome shaped portions have a diameter of about 5 to about 20 nm.

6. The intervertebral disc of claim 4, wherein at least one of the dome shaped portions has a diameter less than a diameter of the core.

7. The intervertebral disc of claim 4, wherein the convex central portion of the upper plate is raised relative to a generally planar peripheral portion of the upper plate.

8. The intervertebral disc of claim 1, wherein the upper vertebra contacting portion and the lower vertebra contacting surface are titanium plasma sprayed.

9. A method of implanting an intervertebral disc between adjacent vertebrae in place of a damaged disc, the method comprising:

providing the intervertebral disc including:

an upper plate having an upper vertebra contacting portion and a lower bearing surface portion, wherein the upper plate is made of PEEK, a lower plate having a lower vertebra contacting surface and an upper bearing surface, wherein the lower plate is made of PEEK, and a rigid core positioned between the upper and lower plates, the core configured to slide and translate over the upper bearing surface and the lower bearing portion, wherein the rigid core is ceramic;

grasping the upper and lower plates of the disc with an instrument by simultaneously grasping the plates at grooves to hold the plates in a locked orientation; and inserting the intervertebral disc between the adjacent vertebrae with the upper and lower plates held in the locked orientation by the instrument wherein the upper vertebral contacting portion and the lower vertebral contacting portion include three finlets on opposing sides of the fin, wherein the finlets extend in height greater than teeth positioned on the upper vertebral and lower vertebral contacting portion, and each finlet includes top surface, wherein each of the finlets have an anterior surface formed at an angle of about 70 to 90 degrees, preferably about 80 degrees, a posterior surface formed at an angle of about 50-70 degrees, preferably about 60 degrees, and the top surface formed at an angle of about 2-20 degrees, each with respect to the upper and lower vertebral contacting portions.

10. The method of claim 9, wherein the upper vertebra contacting portion includes a metal and the lower bearing surface portion includes an MRI compatible material.

11. The method of claim 9, further comprising a plurality of teeth on the upper vertebra contacting portion of the upper plate and the lower vertebra contacting surface of the lower plate.

12. The method of claim 9, wherein each of the upper plate and the lower plate include a convex central portions that are dome shaped portions.

13. The method of claim 12, wherein the dome shaped portions have a diameter of about 5 to about 20 nm.

14. The method of claim 12, wherein at least one of the dome shaped portions has a diameter less than a diameter of the core.

15. The method of claim 12, wherein the convex central portion of the upper plate is raised relative to a generally planar peripheral portion of the upper plate.

16. The method of claim 9, wherein the upper vertebra contacting portion and the lower vertebra contacting portion are titanium plasma sprayed.

* * * * *